(12) United States Patent
Melton, Jr. et al.

(10) Patent No.: US 6,514,220 B2
(45) Date of Patent: Feb. 4, 2003

(54) NON FOCUSSED METHOD OF EXCITING AND CONTROLLING ACOUSTIC FIELDS IN ANIMAL BODY PARTS

(75) Inventors: Hewlett E. Melton, Jr., Sunnyvale, CA (US); James T. Fearnside, Lexington, MA (US); Claudio I. Zanelli, Menlo Park, CA (US)

(73) Assignee: Walnut Technologies, Boston, MA (US)

( * ) Notice: Subject to any disclaimer, the term of this patent is extended or adjusted under 35 U.S.C. 154(b) by 86 days.

(21) Appl. No.: 09/769,551

(22) Filed: Jan. 25, 2001

(65) Prior Publication Data

US 2002/0099324 A1 Jul. 25, 2002

(51) Int. Cl.[7] .................................................. A61H 1/00
(52) U.S. Cl. ........................... 601/2; 600/437; 600/439; 600/442
(58) Field of Search ................................ 600/437–461; 601/2

(56) References Cited

U.S. PATENT DOCUMENTS

| | | | | |
|---|---|---|---|---|
| 3,477,422 A | * | 11/1969 | Jurist, Jr. ..................... | 600/552 |
| 3,847,141 A | * | 11/1974 | Hoop ......................... | 600/437 |
| 4,966,131 A | * | 10/1990 | Houghton et al. ...... | 310/316.01 |
| 5,309,898 A | * | 5/1994 | Kaufman et al. ........... | 128/925 |
| 5,545,124 A | * | 8/1996 | Krause et al. ................... | 60/2 |
| 5,547,459 A | * | 8/1996 | Kaufman et al. ........... | 600/439 |
| 5,720,290 A | * | 2/1998 | Buhler et al. ................ | 600/449 |

* cited by examiner

Primary Examiner—Marvin M. Lateef
Assistant Examiner—Barry Pass
(74) Attorney, Agent, or Firm—Cesari and McKenna, LLP

(57) ABSTRACT

The effect of ultrasound irradiation of a human or other animal body portion is enhanced by operating the body portion as a trapped mode resonator. The intensity and location of resonances within the body portion is controlled by controlling such variables as the amplitude, frequency and/or phase of the ultrasound irradiation. This minimizes the overall energy required to be applied to the body portion in order to achieve a desired localized intensity level.

10 Claims, 8 Drawing Sheets

NON FOCUSSED METHOD OF EXCITING AND CONTROLLING ACOUSTIC FIELDS IN ANIMAL BODY PARTS

BACKGROUND OF THE INVENTION

1. Field of the Invention

The invention relates to the treatment of animal bodies by means of ultrasound, and comprises a method and apparatus for creating intense acoustic pressures interior to selected portions of an animal body without the need for focusing the incident acoustic radiation.

2. Background Information

Ultrasonic energy, applied to a selected region within a body from an extracorporeal transducer, is often used as a therapy means. Examples include ultrasonic ablation of tissue as shown, e.g., in U.S. Pat. No. 4,858,613, "Localization and Therapy System for treatment of spatially oriented focal disease", issued Aug. 22, 1989, to Fry et al.; fracture of kidney stones, as shown, e.g., in U.S. Pat. No. 4,539,989, "Injury Free Coupling of Therapeutic Shock Waves", issued Sep. 10, 1985 to Forssmann et al; heat therapy, as shown in, e.g., U.S. Pat. No. 4,586,512, "Device for Localized Heating of Biological Tissue, issued May 6, 1986 to Do-huu; and destruction of thrombi, as shown, e.g., U.S. Pat. No. 5,509,896 "Enhancement of Sonothrombolysis with External Ultrasound, issued Apr. 23, 1996 to Carter et al. The mechanisms of action for these applications require acoustic intensity levels sufficient to cause significant heating or mechanical disruption or destruction of tissue preferably only within a localized region.

The acoustic intensities used for treatment in the localized region of the body range from 0.5 to 100's of watts per $cm^2$ at the internal treatment site, at frequencies in the 100 kHz–2 MHz range. Prolonged exposure to intense acoustic fields causes tissue destruction through heating or mechanical action. Thus, it is important that the acoustic field be controlled so that only the target tissue receives prolonged exposure. Ultrasonic energy that passes through intervening layers of energy-absorbing tissue, like the skull, in order to reach the area targeted for treatment can cause heating in those intervening layers. Bone absorbs ultrasound at least thirty times more readily than brain tissue; thus, to avoid undue skull heating, acoustic intensities at the skull must be kept low.

The acoustic field at the skull can be shaped by geometric focusing, using either physical or electronic lenses to avoid undue skull heating. FIG. 1 illustrates this type of system. Ultrasound transducer 100 contains a lens structure 110 that produces a concave shaped wave front 120 that converge along paths 130 to a point of intended focus 175 after transiting the skull 125. The acoustic intensity at the convergence point 175 is many times higher than it is at the penetration area 150 of skull 125.

Geometric focussing becomes impractical when low frequency ultrasound is used, because physically large, impractical transducers and lenses are required. In such cases, low frequency ultrasound, below 100 kHz, may be used in combination with a lytic agent such as tissue plasminogen activator (tPA); the low frequency ultrasound increases the thrombolytic rate of the tPA. See, e.g., Suchkova, V et al "Enhancement of Fibrinolysis with 40 kHz Ultrasound", *Circulation:* 1998, pp. 1030–1035. However, at this frequency, a geometrically focussed system requires transducers and lenses of 25 cm diameter or larger in order to provide a moderate degree of focussing. Such large transducers require liquid coupling media between the transducer/lens structure, and the subject tissue in order to efficiently couple acoustic waves into the tissue. Since bone is characterized by different sound velocities than either the coupling media or the target brain tissue, complex lenses that can correct for local variations in refractive index are used. Measurements of skull thickness and a map of refractive index over the entrance surface of the ultrasound are then required in order to compute the necessary shape of the lens. This leads to a complicated and large ultrasound system.

Another disadvantage of a lens based system is that there is no built in safety factor should the wrong lens or acoustic power levels be inadvertently used. Inertial cavitation, which arises in liquids in the presence of high acoustic intensity levels, is known to damage living tissue, and therefore should be avoided.

SUMMARY OF THE INVENTION

It is an therefore an object of this invention to provide an improved system that delivers the desired acoustic energy within a living being without employing cumbersome, large lenses with their unwieldy coupling components, while keeping the applied acoustic intensities at acceptably low levels at non target tissue sites.

It is further an object of this invention to provide a system that delivers the desired acoustic energy within a living being, but does not require a measurement of tissue thickness in order to do so.

Still a further an object of this invention is to provide a system that delivers the desired acoustic energy within a living being, but which does not require a measurement of refractive index in order to do so.

Yet another object of this invention is to provide a system that does not require that the shape of a lens, either physical or electronic, be varied in order to compensate for local refractive index variations within a living being.

Yet another object of this invention is to provide a system which includes a method to spatially position a region of therapeutic acoustic intensity within a desired region of a selected volume.

Yet another object of this invention is to provide a system which includes a method of placing a region of therapeutic acoustic intensity in a predetermined location within a selected volume.

We have observed that many body structures act as resonators. The brain vault, for example, is bounded by layers of differing acoustic impedance, thereby causing reflection of acoustic waves at these boundaries. At frequencies in the 0–500 kHz range, there is little attenuation of longitudinal acoustic waves in the brain or skull, and if reflection at a boundary layer is near total, then acoustic waves pass back and forth through tissue many times creating a trapped mode resonator.

FIG. 2 illustrates the acoustic field in such a resonator. Ultrasound transducer 200 emits wave fronts 250 that transit the skull 225. Due to low acoustic loss in the tissue 235 in the cranial vault, the waves travel to the other side of the skull, where they are reflected as wave 255 due to the differing acoustic impedance of the bone and air which forms the skull and its outside boundary. These reflected waves 255 again travel across the cranial vault and again are reflected by the bone and air interfaces, and return across the cranial vault. This process is repeated many times, and builds up to the point where the internal acoustic energy losses in the cranial vault and the reflections at the skull balance the acoustic energy applied by transducer 200. At points 280 where the acoustic waves intersect, pressure nodes and anti-nodes are formed, depending on whether the wave fronts interfere out of phase or in phase, respectively. A common measure of the resonant property of a system is its quality factor, defined as $2\pi$ times the ratio of stored energy to the lost energy per cycle. In practice, we have measured Q's of from 10 to more than 100 in isolated skull experiments, with node to anti-node pressure ratios of from 10 to more than 100.

We make use of this fact by treating a body part that is to be subjected to acoustic waves below 500 kHz, and preferably below 100 kHz, as a trapped mode resonator. Such a resonator can exhibit a high Q (e.g., a Q of 10 or more) at certain frequencies that cause wave front interference from multiple reflections to add up in phase. Examples of trapped mode resonators within a body include (a) the cranial vault bounded by air, bone and neck tissue; (b) arms; (c) legs; and (d) the thorax, all of which are bounded by air and other tissues. In high Q resonators, very high pressures can be achieved in the resonator cavity for very modest input power U. The differing impedance of skull and air from brain assures that there will be internal reflections, thereby causing the cranial vault to act as a resonator. At frequencies below 500 kHz, little acoustic power need be delivered to the skull to maintain the acoustic field in the brain, because there is little skull or brain heating caused by absorption or other losses The amount of energy, W, stored in the resonator at a given frequency is a function of the frequency; thus to maximize the pressure field, the cavity must be "tuned" to a frequency which maximizes W. In accordance with a first embodiment of the invention, we vary the exciting frequency in accordance with the average pressure at the region of interest is found. Typically, we seek to maximize this pressure. The pressure field at the skull surface may be used as a proxy for the pressure field within the cranial vault, so that a surface transducer may be used to indirectly monitor the pressure within the region of interest and thus the stored energy, W. The surface pressure measurement may be made either by dedicating to this purpose one or more transducers attached to the resonator surface, or by momentarily turning off the electrical drive to one or more elements of exciting transducers and using them in a receive mode.

In accordance with a second embodiment of the invention, we maintain a high Q in the region of interest in the cavity by varying the driving frequency in accordance with the acoustic impedance of the cavity as seen by the driving transducer. Typically, we seek to maximize this impedance. The cavity impedance will be a local maximum at each frequency where the Q of the cavity reaches a local maximum. The cavity impedance can be calculated if the relationship between the electrical impedance of the transducer and the acoustic load impedance applied to the acoustic port of the driving transducer is known. Often a transducer can be treated as a three port network, containing two acoustic ports and one electrical port. In this case, the impedance of any port can be expressed in terms of the physical characteristics of the transducer, and the acoustic load impedance on each of the other two ports.

In accordance with a third embodiment of the invention, we excite the cavity with a short pressure pulse, h(t), via a broadband transducer placed in contact with the skull, e.g., a transducer that emits a pulse whose frequency components preferably lie primarily (as determined, e.g., by its 3-db points) within a range of from about 20 kHz to about 40 kHz.

The Fourier transform of the pressure pulse h(t) is H(f) and it contains a multiplicity of frequency components. The acoustic response of the resonant cavity is recorded by monitoring the time response g(t) of the pressure at the surface of the skull, either with the same transducer acting as a receiver, or with another broadband transducer. The time pressure waveform, g(t), is then converted to its frequency domain equivalent $$G(f) = \Im(g(t))$$

Those frequencies f1 ... fn in G(f) where peaks in the amplitude response of G(f)/H(f) occur correspond to resonant frequencies of the cavity. By controlling the Q's corresponding to these resonant frequencies, the positions of the maxima and minima of the waveforms at the respective frequencies may be controlled by the user to thereby control the energy in a given region. Specifically, they may be positioned at desired specific sites within the cavity to thereby intensify the acoustic pressure at those sites without the use of acoustic lenses or the like, and may readily be moved about within the cavity under control of the user simply be controlling one or more characteristics of the electrical signals driving the acoustic transducers.

The Q of a resonator varies proportionally to the reciprocal of the internal losses in the resonator. Internal losses may vary because of changes in the absorption of acoustic energy within the material that fills the resonator cavity, such as due to the onset of cavitation. Should cavitation occur, the Q of the cavity decreases due to energy absorption by the oscillating cavitation bubbles. Provided that the energy, U, supplied to the cavity by the acoustic driving source is substantially constant, the acoustic pressures within the cavity decrease as cavitation occurs, thereby retarding the cavitation process.

The Q of the resonator can be estimated by observing the build up time or decay time (ring-down time) of the pressure field within the resonator. Build up time is the time taken for the acoustic field to reach approximately 63% of it's final value. The decay time is the time taken for the acoustic field to decay to approximately 1/e (approximately 37%) of its initial value. Therefore by exciting the resonator cavity (e.g., a patient's skull) with one or more exciting transducers, and measuring the build up time or, after build up has completed, turning the exciting transducers off and measuring the decay time, Q can be estimated using the approximation:

$$Q \sim 3.12 f/\alpha$$

where f is the desired frequency;

$\alpha$ is the reciprocal of either the buildup or decay time.

As acoustic waves within the resonator are being reflected back and forth within the cavity, pressure nodes and anti-nodes are found within the cavity which correspond to places where destructive and constructive interference of the acoustic waves occur. Further in accordance with the present invention, the location and magnitude of the nodes and anti-nodes are controlled by adjusting the magnitude and/or phase of the waves within the cavity, in addition to varying the frequency as earlier described. One or more of these parameters may be controllably varied in order to achieve a desired placement and intensity of pressure maxima and minima within a cavity.

At any point within the resonant cavity, the time function of pressure can be described as:

$$P(t) = \Sigma P_i \exp(\omega_i t + \Phi_i)$$

Where

P(t)=the instantaneous pressure at time t;

$P_i$=the peak pressure of the ith pressure wave;

$\omega_i$=the i-th pressure waveform frequency at a time t, in radians/sec;

$\Phi_i$=the relative phase delay of the i-th pressure waveform at time t. Phase delay is a function of both the position of the transducer used to introduce the i-th pressure wave into the cavity, and also the phase of the driving signal for the transducer relative to an arbitrary reference;

$\Sigma$ represents the summation operation over all pressure waveforms at time t that exist at this point within the cavity.

If all pressure waveforms have the same frequency, $\omega$, the resultant waveform is a standing wave of that frequency, whose amplitude is the vector sum of all of the individual pressure waveforms. A vector sum that is a minimum corresponds to a pressure node and a maximum sum vector corresponds to an anti node. The location of these nodes and anti-nodes can be controlled, therefore, by controlling $\omega_i$, $\Phi_i$, or $P_i$ for some or all of the pressure waveforms. If the relative phase, frequencies and pressure amplitudes of all of the component waveforms are constant in time, then the locations of the pressure nodes and anti-nodes within the cavity are fixed. If any of $\omega_i$, $\Phi_i$ or $P_i$ are not constant in time, the locations of the pressure nodes and anti anti-nodes move within the cavity over time. It should be noted that $\Phi_i$ can be varied either by varying the phase of a signal driving a transducer, or by moving the active transducer aperture. The active transducer aperture is that portion of the transducer which is radiating or receiving acoustic energy. The active aperture may be moved electronically, by exciting different portions of one or more transducers at different times.

Pressure nodes and anti-nodes can be placed in known positions within the resonator or moved about so that these nodes and anti-nodes remain in one part of the cavity only for a predetermined period. To place a set of nodes and anti-nodes at some predetermined location, any of $P_i$, $\Phi_i$, and $\omega_i$ can be adjusted. A preferred method is to adjust $\omega_i$ to achieve a peak pressure response within the cavity, and then adjust $\Phi_i$ to place the set of nodes and anti-nodes as needed. Moving pressure nodes and anti-nodes in time has the advantage of retarding or suppressing local heating and /or cavitation.

DETAILED DESCRIPTION OF AN ILLUSTRATIVE EMBODIMENT

Figure 1:
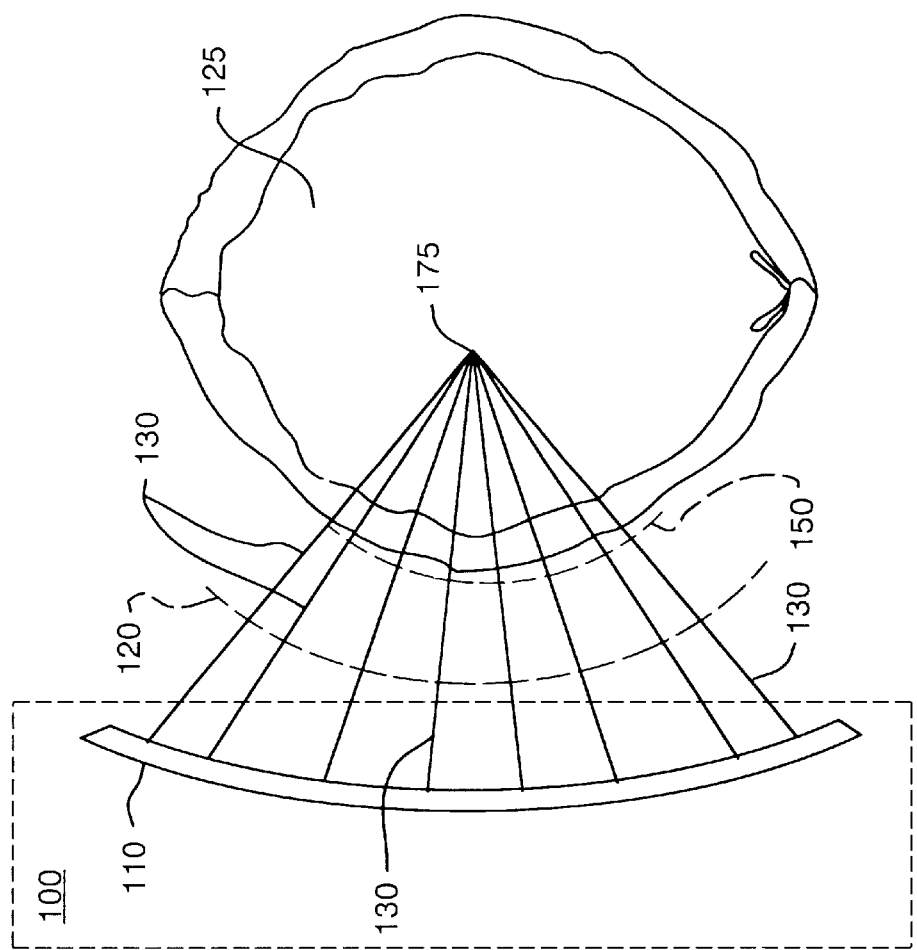
FIG. 1 (Prior Art) depicts a cross section of skull, and a geometrically focussed transducer to achieve high intensities somewhere within it.
Figure 2:
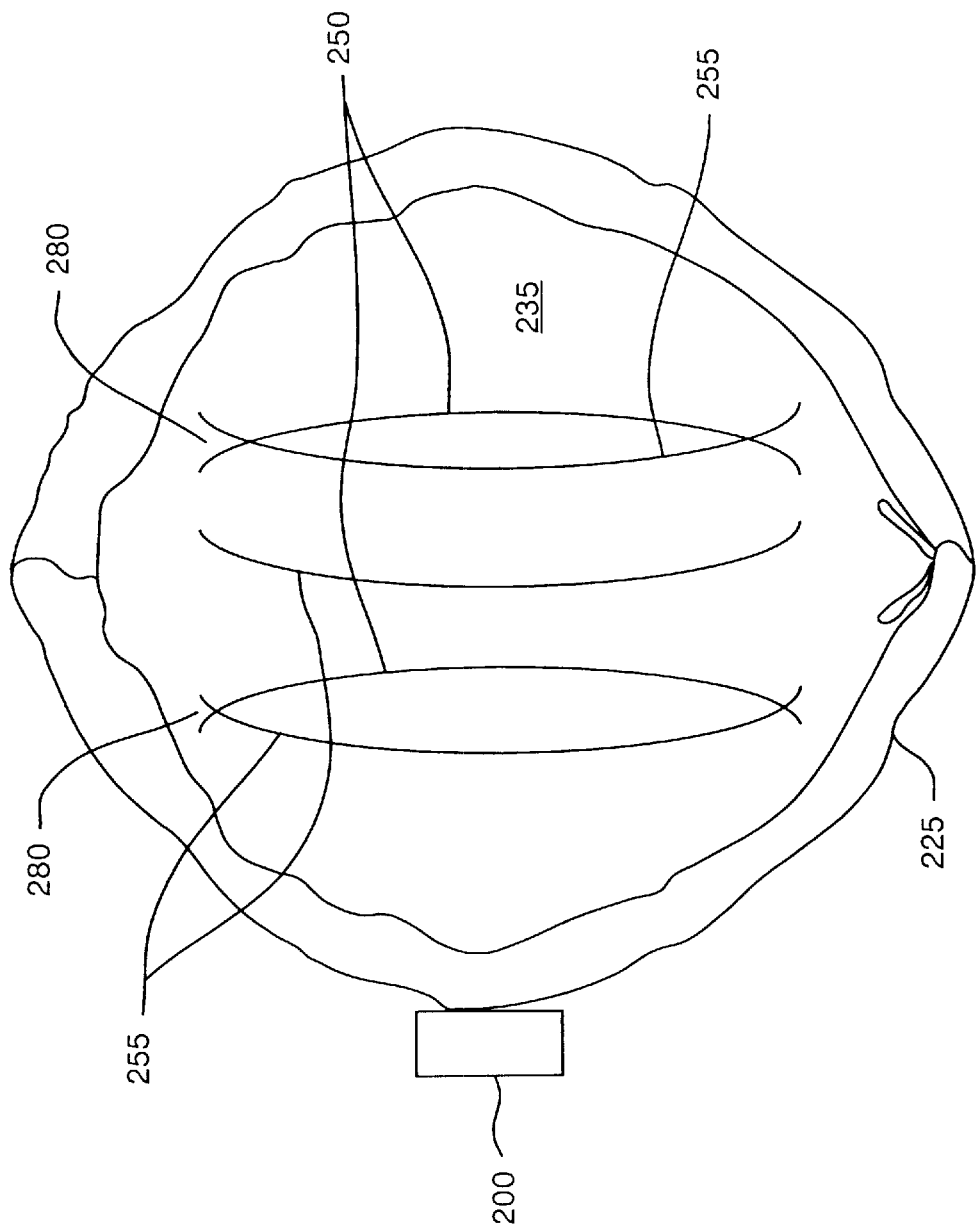
FIG. 2 depicts a plan view of a cranial vault, showing the interference pattern that is generated by acoustic waves being reflected back and forth within the cranial vault.
Figure 3A:
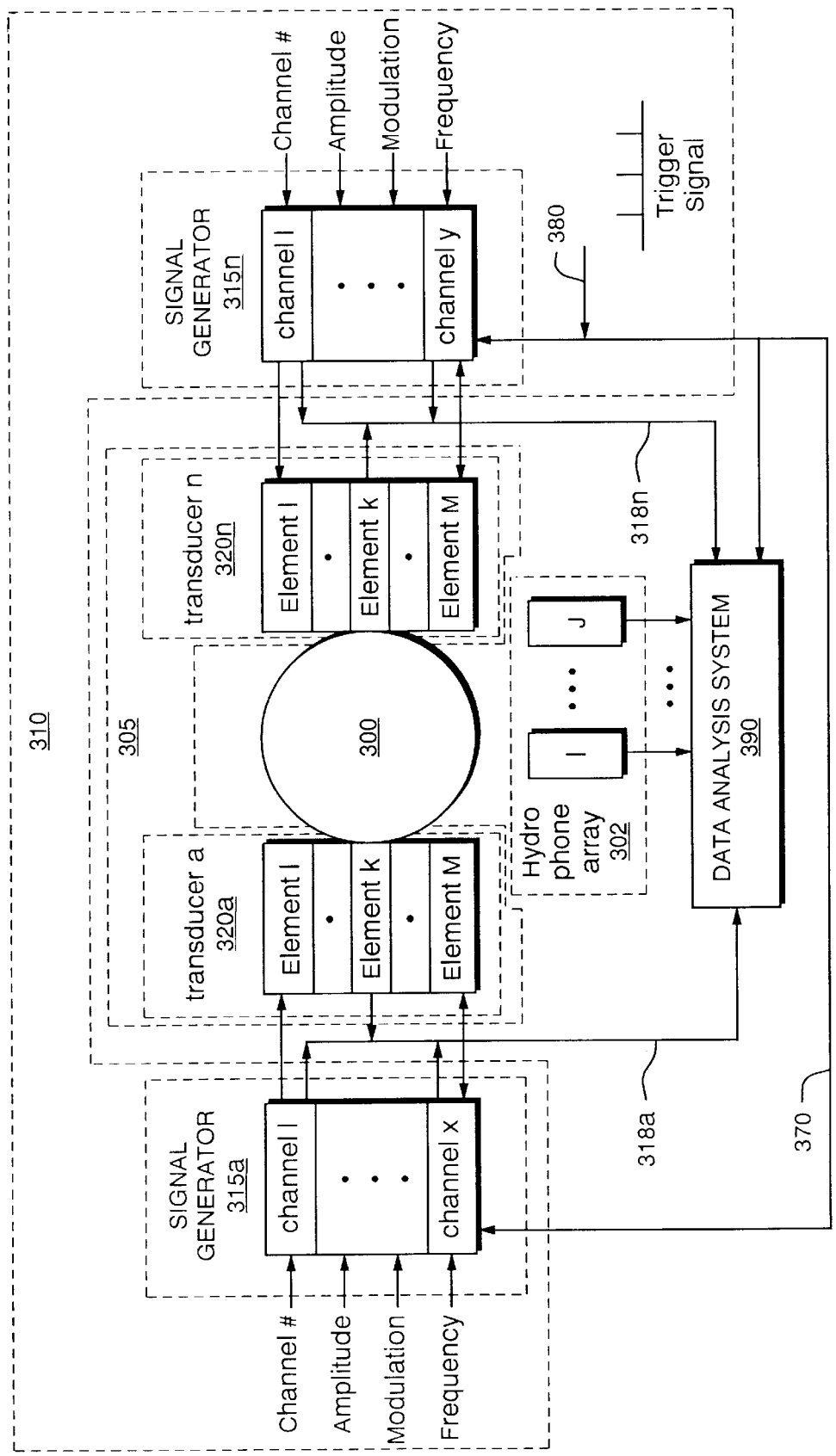
FIG. 3a depicts a block diagram of a preferred embodiment of the invention.

FIG. 3a is a block diagram of an apparatus that operates in accordance with the invention. Acoustic generator 305 consists of transducers 320a . . . n that are placed in contact with the body part 300 that is to be excited as a resonator. Each transducer consists of one or more transducer elements 320a1 . . . M, and 320n1 . . . L as shown on the diagram. Transducer element 320a1, for example, may be used exclusively as a transmitter, i.e. it is used only to transmit acoustic energy into the body. Transducer element 320ak, for example, may be used as a hydrophone, i.e. it may be used only to receive acoustic energy. Transducer elements 320aM and 320nL may be used bidirectionally, i.e. they both transmit and receive acoustic energy.

Acoustic generator 305 is connected to a generator signal source 310. Generator signal source 310 is composed of one or more signal sources 315a . . . x, up to one for each transducer 320a . . . n. Each transducer signal source may have one or more output channels e.g. signal generator 315a has channel 1 . . . channel x. These channels are connected to transmitter transducer elements or to bi-directional transducer elements or to both, and are also connected to a signal bus, 318a . . . n. Transducer Elements k, which are used as hydrophones, are not typically connected to a signal generator, but are connected to a signal bus 318a . . . n. Measurements of impedance and also power for any element may be made by data analysis system 390 which is also connected to these signal busses.

For each output channel of a transducer element's signal source 315a . . . 315n, the drive signal amplitude, modulation characteristics, signal waveform type, and frequency may be independently specified. Trigger signal 380, shown as a train of synchronizing pulses, but which may be some other synchronizing signal, is generated within signal source 310 and synchronizes the signal generators 315a . . . n and also the data analysis system 390, via buss 370. The system also includes an array of hydrophones 302, consisting of k independent hydrophones which are placed in contact with the body part that is to driven as a resonator. These hydrophones are also connected to the data analysis system 390, so that their outputs can be analyzed.

Figure 3B:
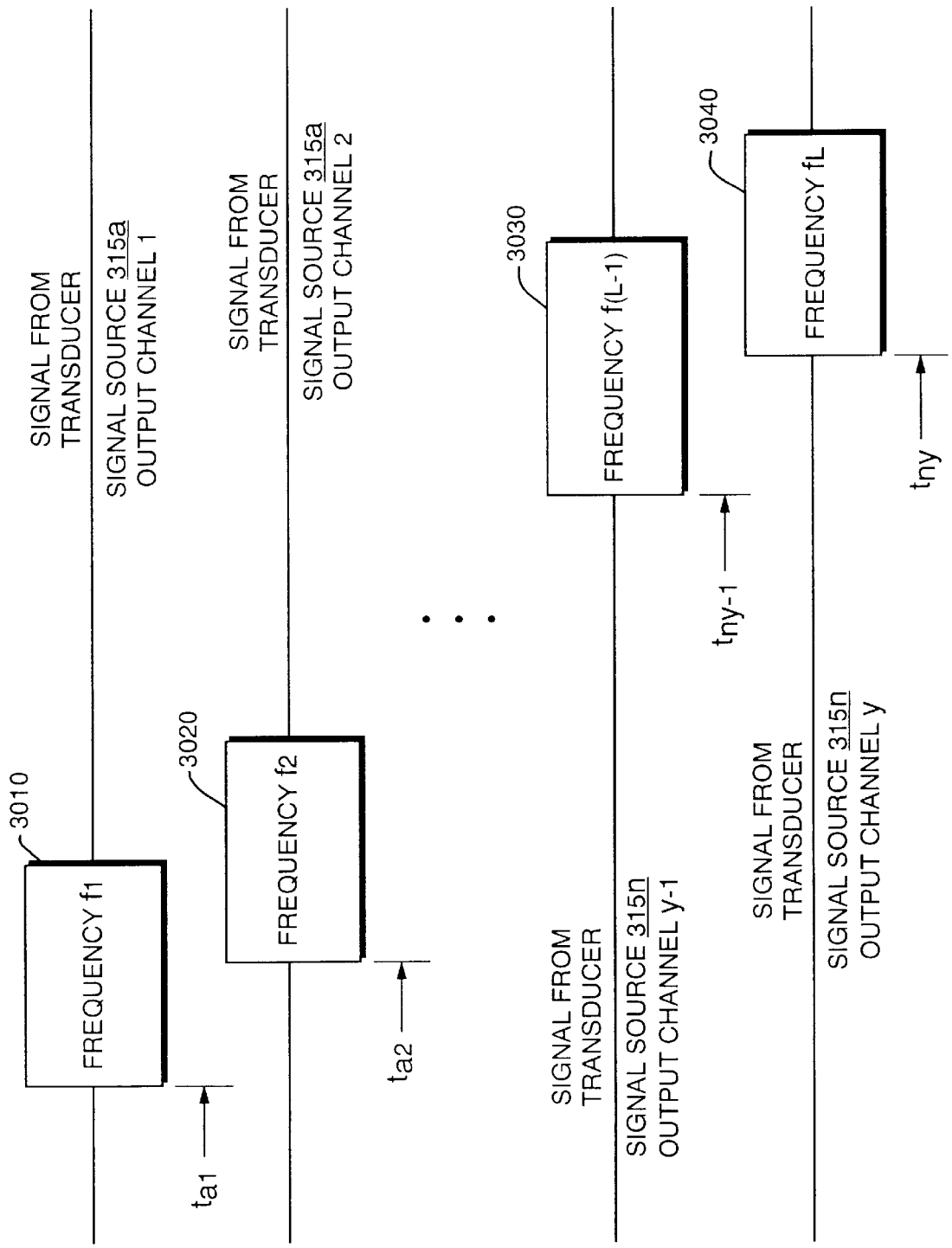
FIG. 3b illustrates one type of modulation that results in aperture shifting.

Placement and movement of the nodes and anti-nodes within the resonator are controlled by controlling the amplitude, frequency or phase, or any combination thereof for one or more transducer signal generator output channels. It is specifically noted that amplitude modulation may be used to electronically move one or more active apertures, which also moves the locations of the nodes and anti-nodes within the resonator. For example, referring to FIG. 3b, signal bursts 3010, 3020, 3030, 3040 are shown. These are tone bursts which are generated by amplitude modulating each carrier signal f1 . . . fn1 by the appropriate envelope, e.g., a rectangle function, delayed by that appropriate delays t1 . . . tn1. By making the delays unequal, different elements are turned on at different times. Since the active aperture at any time is composed of only those elements that are being excited, the active aperture is moved electronically, thereby moving the positions of the nodes and anti-nodes within the resonator.

As discussed above, the signal generators 315 provide electrical driving signals for the acoustic transducer drivers 320. These signals may comprise, e.g., sinusoidal waves of defined amplitude, frequency, phase or waveshape; or may comprise pulses of defined amplitude and duration. The signal generators may comprise self-contained units in which the control variables (amplitude, frequency, phase, pulse height, pulse duration, waveshape, etc.) are set by the user by manipulating control knobs that set the control variables; or may be responsive to a control program, stored either internally within the system or externally to it, which defines and controls the desired parameters. Signal generators of both types are known and, indeed, are commonly available as commodity items.

As illustrated in FIG. 3a, we prefer to control the driving signals of signal generators 315 from an external programmed controller and data analysis system 390. Preferably the system 390 comprises a programmable data processor, e.g., a "Personal Computer" into which the user may enter a control program specifically prepared by him/her to control the variables of interest for the particular treatment or experiment. Preferably, the control program enables the user to vary the driving parameters in real time, if desired, to accommodate specific patient or experimental conditions. To facilitate positioning of the nodes and anti-nodes, a joystick is advantageously coupled to the controller for rapid change of one or more of the control parameters, and a video monitor is provided on which the region of interest is displayed showing either the actual location of an acoustic maxima or a computed location in accordance with the specific control parameters characterizing the signal generator output as any given moment. The system 390 may also serve to analyze data generated during the treatment or experiment.

The arrangement of FIG. 3 provides the maximum flexibility in positioning and controlling the energy maxima and minima with a desired region of a skull or other body cavity. A simplified system is set forth in FIG. 4a which shows an embodiment of the invention used to place acoustic fields inside a human skull, with the cranial vault being the resonant cavity. This embodiment contains a hydrophone 415 and transmitter 420 which are each comprised, e.g., of a single element. Alternatively, transducer 420 may be used as both a transmitter and a receiver (hydrophone) without requiring transducer 415. Transducer holder 410 is mounted on the head 400 of a subject. Transducers 415 and 420 are mounted in transducer holder 410 such that they are pressing on opposite sides of the head 400 above the ear. Cable 430 leads to the system electronics 435 connected to the transducer.

Figure 4A:
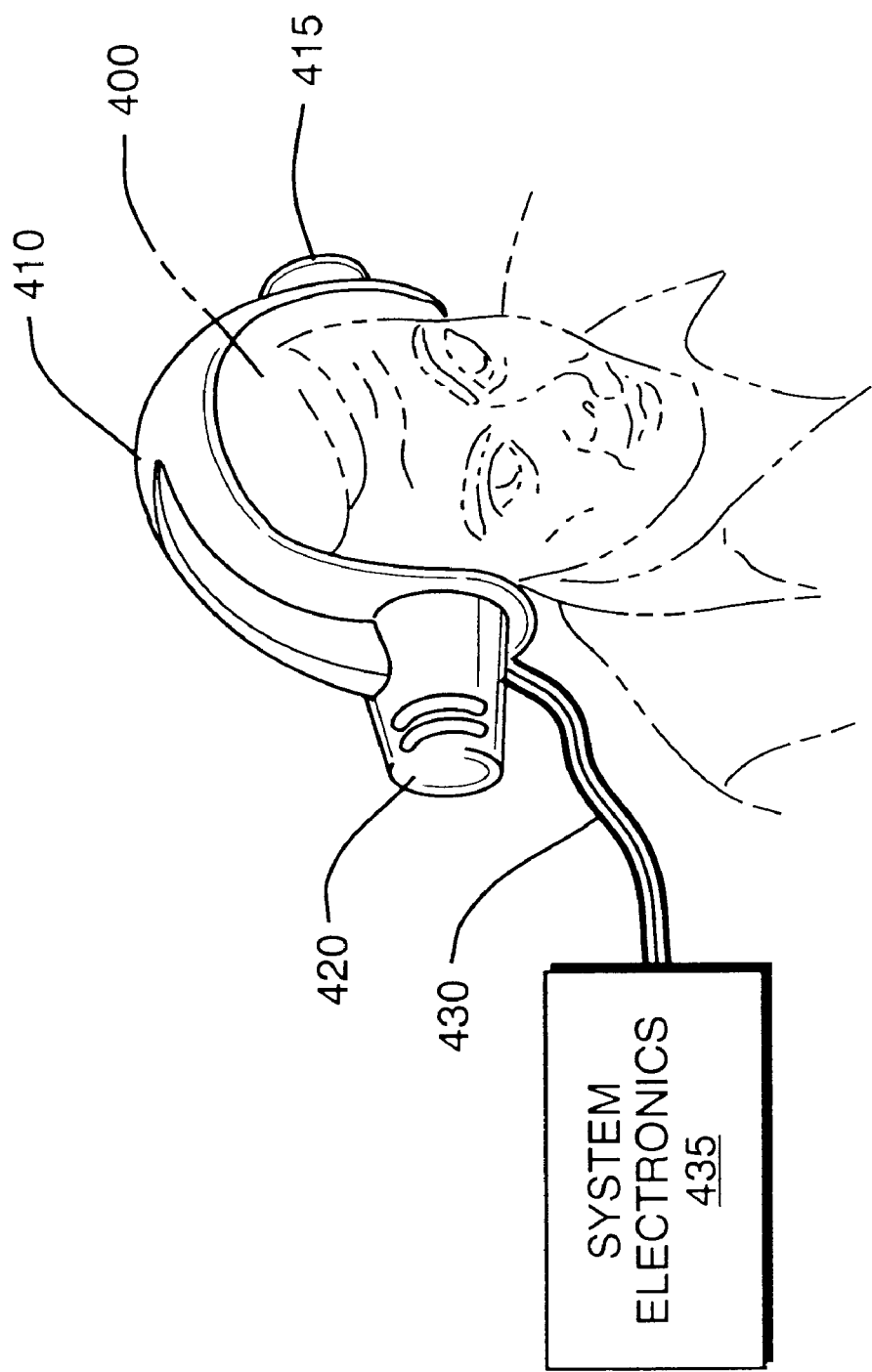
FIG. 4a shows the present invention embodied in a headset, connected to system electronics via a cable.
Figure 4B:
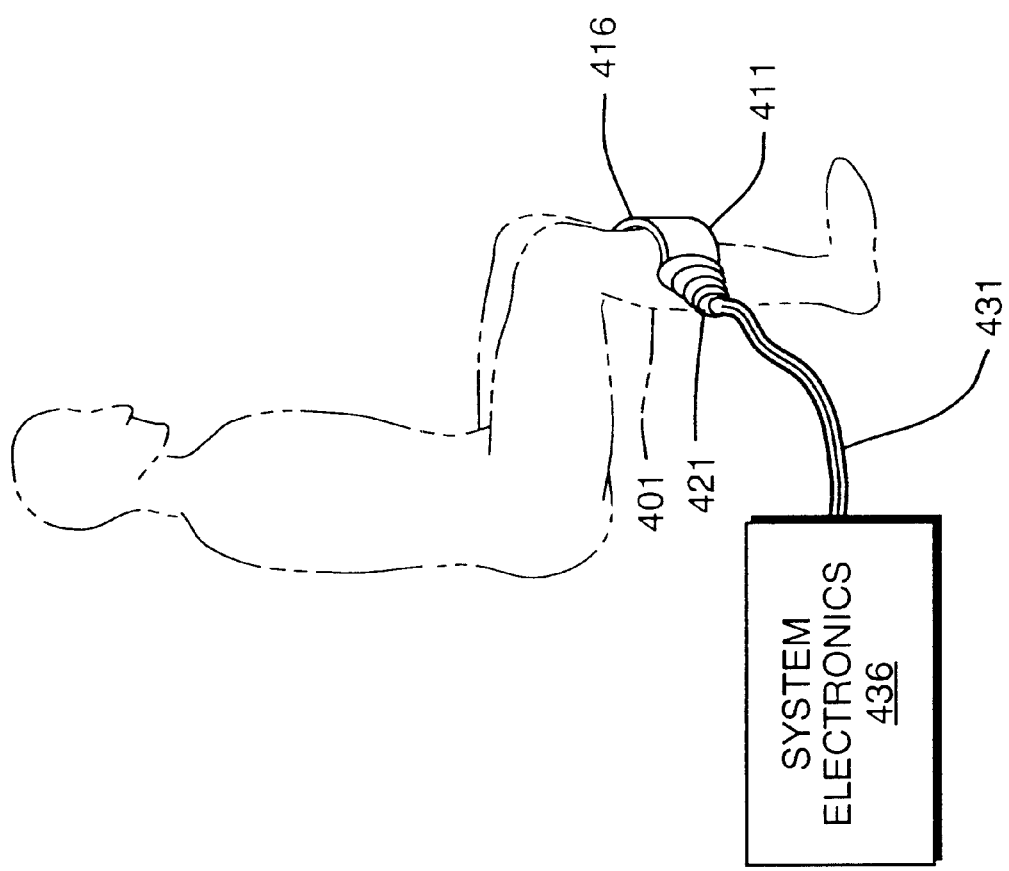
FIG. 4b shows the present invention embodied in a clip, connected to system electronics via a cable.

FIG. 4b depicts an embodiment of the present invention applied to a body appendage, in this case a lower leg which is the resonant structure. Transducer holder 411 is mounted on the lower leg 401 of a subject. Receiving transducer 416 and exciting transducer 421 are mounted in transducer holder 411 and are pressed against opposite sides of the leg. Cable 431 leads to the system electronics 436.

Figure 5:
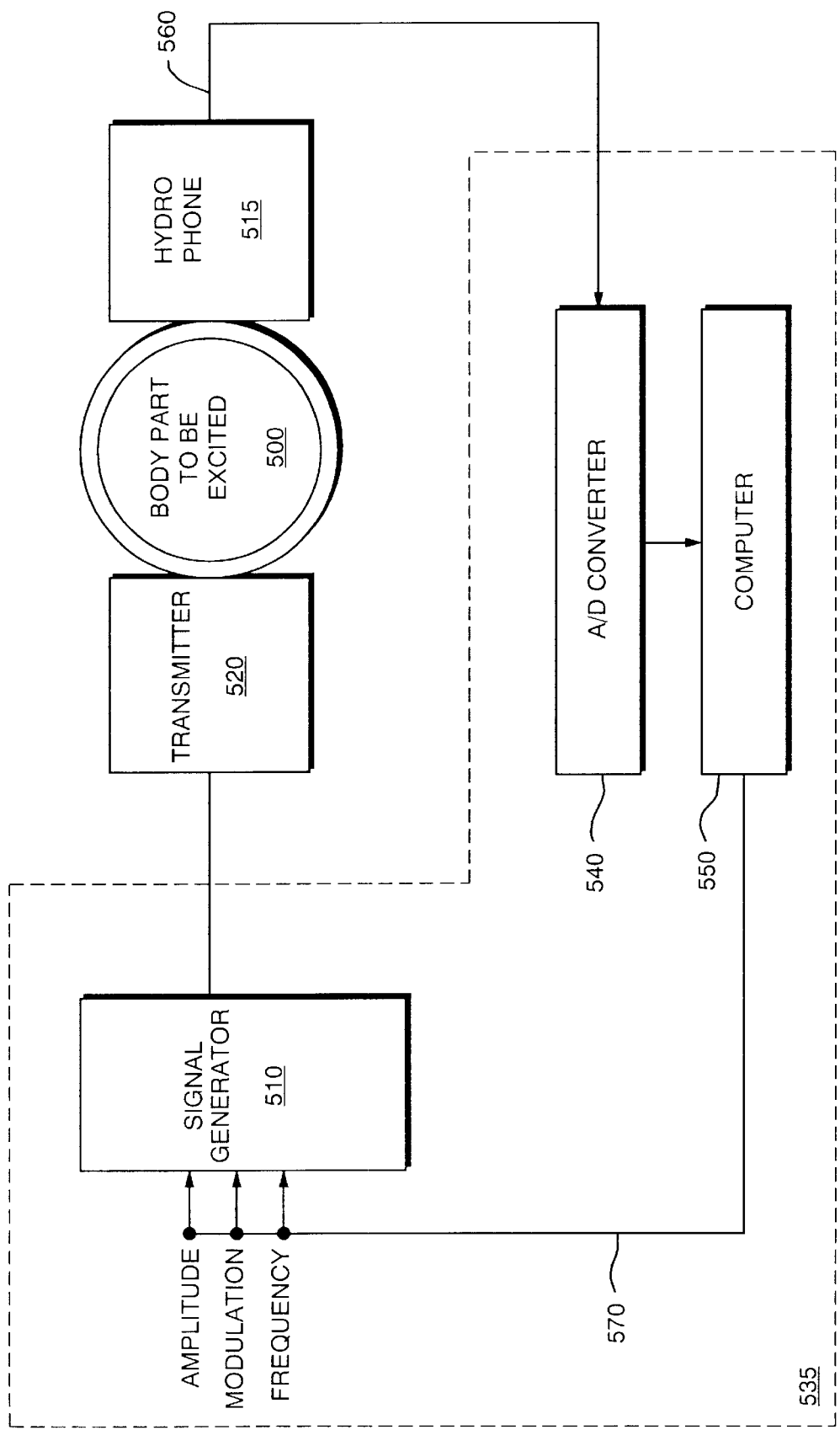
FIG. 5 depicts the block diagram of a dual transducer version of the preferred embodiment.

FIG. 5 is the block diagram of the physical embodiment depicted in FIG. 4a. Single element transducers 515, 520 are placed in contact with head 500 and are electrically connected to system 535. System 535 consists of signal source 510, A/D converter 540, and computer 550. Computer 550 is programmed to control the frequency, amplitude, and modulation of signal source 510 via bus 570 The program may be selectable under control of the user or may comprises a fixed program. In accordance with the invention, the modulation can be any of amplitude, phase, frequency or pulse width. The drive waveform can be any repetitive waveform. Hydrophone 515 is connected to A/D converter 540 via connection 560, thereby allowing the pressure at the surface of the resonator as seen by the hydrophone to be read.

Initially computer 550 controls transducer signal generator 510 via bus 570 to a pre defined lower frequency limit, $f_{min}$, approximately 20 kHz, and the transducer is stepwise swept through a selected frequency band to a high limit fmax, approximately 40 to kHz, to find peaks in the ring down time within this selected band. The frequency increment, $\Delta f$, is selected by the program or by the user based upon the minimum frequency $f_{min}$ of the frequency band to be swept, and the expected maximum Q (100 in the case of the human skull) of the resonator. For example, the selection may be made in accordance with the formula $\Delta f \sim f_{min}/(Q*5)$. Other methods of calculating $\Delta f$ may be used, provided they detect the peaks in the ring down time of the resonator as measured by hydrophone 515. At each frequency increment within the selected frequency band the acoustic field within the body part 500 is excited by signal source 510 connected to transducer 520 for 50 cycles. After the completion of the 50 cycles of excitation, 50 cycles of the pressure waveform as received by transducer 515 is captured by A/D converter 540. The ring down waveform is of the form:

$$P(t)=P_0\exp(-\alpha t)\cos(2\pi ft+\Phi)$$

Figure 6:
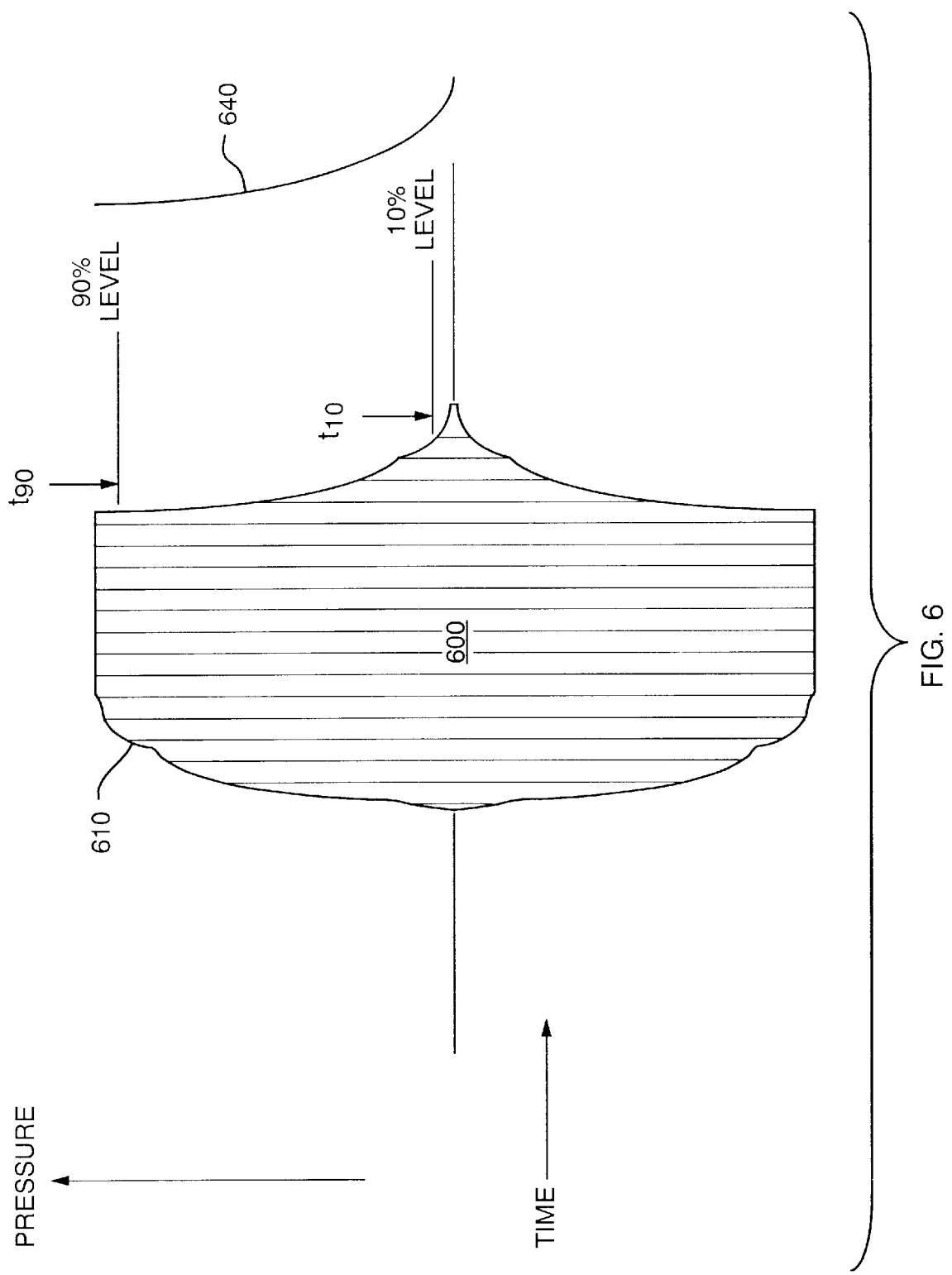
FIG. 6 illustrates the manner in which the Q of the resonator may be determined.

Where:
P(t) is the pressure waveform at the surface of the resonator
$P_0$ is the pressure at time when transducer 520 was switched off at the completion of 50 cycles of excitation
$\alpha$ is the inverse of the time it takes for the envelope of the ring down waveform to reach approximately 37% of its starting value.
f is the frequency of excitation of the resonator
$\Phi$ is a phase constant FIG. 6 depicts the method used to make the measurements required to estimate Q. Waveform 600 which is a tone burst at the frequency, f, supplied by exciting transducer 520, is received by hydrophone 515, and converted to digital form by A/D converter 540. The envelope 610 of the tone burst is extracted, and times too and $t_{90}$ on the trailing edge of envelope 610 are marked that correspond to the 10% and 90% of the maximum amplitude of the envelope. The portion of the envelope between these two points is used to perform a least squares fit to the function $P_0\exp(-\alpha t)$, which is shown schematically as curve 640. $E_0$, the amplitude of the generator 510, $P_0$, f, Q, and $\alpha$ are saved. As noted above, $$Q \sim 3.12 f/\alpha$$

This process is repeated at each frequency step until the entire selected frequency band has been swept. For example, for a one inch diameter longitudinal mode exciting transducer 520, placed over the temporal bone of a water-filled intact human skull, it is found that peaks in Q occurred at 23.6, 23.9, 27.1, 27.4 and 28.0 kHz. A typical a was measured to be 1971 sec-1 at 27.4 kHz, yielding an approximate Q of 43.4. The ratio of pressure, as measured by a 3 mm diameter transducer 515 to the peak pressure at the principle anti-node in the middle of the cranial vault was 10:1. The positions of the pressure nodes and anti-nodes within the resonator differ at differing frequencies, so that specifying a frequency modulation function that results in signal source 510 switching between two different resonator resonance points, e.g. 23.6 and 28 kHz, causes the pressure-nodes and anti-nodes within the resonator to change position and shape each time the driving frequency changes.

What is claimed is:
1. Apparatus for generating an acoustic field in a selected body portion of a living being comprising:
an acoustic generator positionable exterior to a region of said selected portion for injecting acoustic waves into said selected portion, wherein the frequency of said acoustic waves is selectable to cause said selected body portion to resonate with a Q greater than 1, further including means for controlling one or more of the amplitude, frequency or phase of said acoustic generator in order to thereby control the motion of the nodes and anti-nodes of the acoustic field within said selected portion of said living being.

2. Apparatus according to claim 1 which includes a controller for controlling the frequency or frequencies emitted by said acoustic generator in order to thereby select a set of resonant frequencies from one or more resonant frequencies wherein said body portion resonates with a Q greater than 1.

3. Apparatus according to claim 1 which includes means for exciting different combinations of transducer elements at different times.

4. Apparatus according to claim 1 which includes means for monitoring the acoustic field in a selected portion of said being in order to estimate the Q of said selected portion of said being.

5. Apparatus according to claim 4 wherein said means for monitoring the Q of said selected portion of said body measures ring down or buildup time of pressure in said selected portion of said body.

6. Apparatus according to claim 4 wherein said means of measuring said acoustic field is a portion or all of said acoustic generator means.

7. Apparatus according to claim 6 wherein the measurement of said acoustic load includes the measurement of electrical impedance of said acoustic generator.

8. Apparatus according to claim 4 wherein said means for monitoring the Q of said selected portion of said body measurement the acoustic load on said acoustic generator of the selected portion of said body.

9. Apparatus according to claim 4 wherein said means of monitoring the Q of said selected portion of said body measures the pressure response function g(t) of said portion of said body to the application of a pressure pulse h(t) wherein said pressure pulse contains a multiplicity of frequency components.

10. A method of generating spatially localized acoustic pressure anti-nodes in a selected portion of an animal body from an acoustic generator comprising:

positioning an acoustic generator exterior to a region of said body capable of acting as an acoustic resonator;

driving said resonator at a plurality of frequencies chosen to thereby establish standing anti-nodes in said body region.

* * * * *